(12) United States Patent
Carlucci et al.

(10) Patent No.: US 6,867,287 B2
(45) Date of Patent: Mar. 15, 2005

(54) BREATHABLE ABSORBENT ARTICLES COMPRISING CHITOSAN MATERIAL

(75) Inventors: Giovanni Carlucci, Chieti (IT); Achille Di Cintio, Pescara (IT); Antonella Pesce, Pescara (IT); Alessandro Gagliardini, Jesi (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/233,857

(22) Filed: Sep. 3, 2002

(65) Prior Publication Data

US 2003/0023216 A1 Jan. 30, 2003

Related U.S. Application Data

(63) Continuation of application No. PCT/US01/13062, filed on Apr. 23, 2001.

(51) Int. Cl.[7] .......................... A61F 13/15; A61F 13/20
(52) U.S. Cl. ...................... 536/20; 536/1.11; 604/361; 604/375
(58) Field of Search ................. 536/1.11, 20; 604/361, 604/375, 379; 442/394

(56) References Cited

U.S. PATENT DOCUMENTS

| | | | |
|---|---|---|---|
| 5,496,933 A | | 3/1996 | Kelkenberg |
| 5,525,710 A | * | 6/1996 | Unger et al. ................ 536/18.7 |
| 5,599,916 A | * | 2/1997 | Dutkiewicz et al. .......... 536/20 |
| 5,932,495 A | * | 8/1999 | Boney et al. ................ 442/121 |
| 6,383,960 B1 | * | 5/2002 | Everett et al. ............... 442/394 |
| 6,570,054 B1 | * | 5/2003 | Gatto et al. ................. 604/364 |
| 6,663,611 B2 | * | 12/2003 | Blaney et al. .......... 604/385.01 |

FOREIGN PATENT DOCUMENTS

| | | | | |
|---|---|---|---|---|
| EP | 0393825 | * | 3/1990 | ............. C08L/1/02 |
| EP | 0 393 825 A1 | | 10/1990 | |
| EP | 0510619 | * | 4/1992 | ........... A61F/13/15 |
| EP | 0811392 | * | 10/1997 | ........... A61L/15/46 |
| EP | 0 811 392 A1 | | 12/1997 | |
| WO | 08112340 | | 7/1996 | |
| WO | WO 99/32697 | * | 7/1999 | |
| WO | WO 99/61079 A1 | | 12/1999 | |
| WO | WO 99/61079 | * | 12/1999 | ........... A61L/15/46 |

* cited by examiner

*Primary Examiner*—James O. Wilson
*Assistant Examiner*—Ganapathy Krishnan
(74) *Attorney, Agent, or Firm*—Roddy M. Bullock (57) ABSTRACT

The present invention relates to breathable absorbent articles, such as sanitary napkins, pantiliners, nursing pads and baby diapers, having a breathable backsheet, and comprising a chitosan material. Absorbent articles are provided that deliver not only initial high performing breathability but also maintain effective breathability in use as well as high protection level while delivering also effective odor control towards odor associated with bodily fluids.

24 Claims, 2 Drawing Sheets

BREATHABLE ABSORBENT ARTICLES COMPRISING CHITOSAN MATERIAL

CROSS REFERENCE TO RELATED REFERENCES

This is a continuation of International Application PCT/US01/13062 with an International filing date of Apr. 23, 2001.

FIELD OF THE INVENTION

The present invention relates to absorbent articles in particular sanitary napkins and panty liners, which combine the somehow contradictory benefit of high performing breathability and high protection level while delivering also effective malodor control benefits.

BACKGROUND OF THE INVENTION

A more and more important consumer need, which underlies development in the absorbent article field, in particular catamenials, is the provision of products with higher comfort level during use.

One means for providing consumer comfort benefits in absorbent articles is by the provision of breathable products. Breathability has typically concentrated on the incorporation of so called 'breathable backsheets' in the absorbent articles. Commonly utilized breathable backsheets are microporous films and apertured formed films having directional fluid transfer as disclosed in for example U.S. Pat. No. 4,591,523. Both these types of breathable backsheets are vapor-permeable allowing gaseous exchange with the environment. This thereby allows for the evaporation of a portion of the fluid stored in the core and increases the circulation of air within the absorbent article. The latter is particularly beneficial as it reduces the sticky feeling experienced by many wearers during use.

However those skilled in the art are faced with several problems when providing absorbent articles with high breathability. An important drawback associated with the use of breathable backsheets in absorbent articles is the negative effect on the protection level performance, by leakage known as wet through onto the users garment. Although, breathable backsheets in principle only allow the transfer of materials in the gaseous state, physical mechanisms such as extrusion, diffusion and capillary action may still occur and result in the transfer of the fluids from the absorbent core through the backsheet and onto the users garments. In particular, these mechanisms become more dominant if the article is utilized during physical exertion, or for heavy discharge loads or over extended periods of time.

Another need when providing breathable absorbent articles, especially highly breathable absorbent articles, is the control of odorous compounds within the articles.

Malodorous compounds typically present in absorbent articles originate from a number of sources. Firstly, the components of the fluid discharge such as urine, perspiration, lactational fluid, menstrual fluid and blood may themselves contain malodorous compounds. Secondly, malodorous compounds may be generated as a result of the degradation of the components of the fluid discharge. Thus there are a wide range of compounds, which may be present at some time during the use of an absorbent article, which have an associated malodor.

It is believed that due to the very nature of a breathable absorbent article, malodorous compounds contained therein may, similar to air and vapor, be more readily exchanged with the environment. Hence, the malodorous compounds are able to escape from the article and are dissipated into the surroundings. Consequently, it is at least perceived by a number of potential users of absorbent articles that malodorous compounds are more easily detectable from breathable absorbent articles than from non-breathable absorbent articles. The presence and detection of malodorous compounds from absorbent articles is however highly undesirable and may cause the wearer of these articles extreme embarrassment and thus, the prevention of their detection is highly desirable.

Another main problem with breathable absorbent articles is that they function well upon initial use while their breathable properties, especially their air transmission abilities, are drastically decreased upon initial loading these articles with bodily fluids. Since loading these articles with liquid is the ultimate reason for their existence a problem underlying the present invention is to maintain a minimum breathability from the wearer surface of the product through the backsheet during the usual usage period.

It is hence an object of the present invention to identify disposable absorbent articles, which maintain their breathability, especially their air transmission ability, preferably above a critical level, even after loading of the articles. It is further an objective of the present invention to provide this continued performance benefit without impairing on the basic absorption and liquid retention functions of such articles. Yet it is an object of the present invention to provide absorbent articles having not only an initial high comfort level but also effective comfort level upon prolonged wearing time of the articles while providing a high level of protection and effective odor control towards a broad spectrum of malodorous components.

It has now been found that these objects are achieved by providing a breathable absorbent article, particularly by the provision of a breathable backsheet, which article comprises a chitosan material. It has only now been found that the use of chitosan materials in disposable breathable absorbent articles can provide an unexpected benefit in respect to maintaining effective breathability of the articles during prolonged usage conditions.

Chitosan materials have the ability to instantaneously reduce fluid diffusion once they are contacted with bodily fluids, thereby concentrating the storage of acquired fluid in their close proximity. This reduction of internal liquid transport results in reduced surface area of the absorbed fluid (e.g., reduced surface area of the stains of menses in the articles). In other words the presence of a chitosan material in an absorbent article will result in larger area of dry article (pad), which is not soiled by bodily fluids like menses. Advantageously the concentration of the bodily fluid at limited locations on the article will maintain the overall breathability of the article at higher level in comparison to the same article subjected to the same amount of bodily fluid but wherein the bodily fluid is left to diffuse over bigger surface area.

Without to be bound by any theory, this benefit is obtained due to the properties of chitosan material to instantaneously gelify bodily fluids coming into contact with it. The gelification rate of chitosan material is only a few seconds towards bodily fluids, i.e., organic fluids like menses. The positively charged cationic groups of the chitosan materials will interact with negatively charged anionic functionalities present in bodily fluids, like the carboxylic groups of proteins or hydroxylic groups of short chain acids (e.g., butyric acid). This will result in the formation of tri-dimensional net between cationic function of the chitosan materials and such molecules with anionic groups. This rapid physical change of the bodily fluid will instantaneously immobilize it in the article avoiding fluid transfer.

Advantageously the presence of chitosan material, alone or in combination with an anionic absorbent gelling material like polyacrylate, allows to maintain the breathability of the whole article at higher levels as compared to a same article (in structure and materials) which comprises for example only such an anionic absorbent gelling material in absence of chitosan material at the same total level.

The purpose of the present invention is preferably achieved when the breathability of an absorbent article as measured by the air permeability of the article expressed in l/m2/s, after absorption of 2 ml of artificial menstrual fluid, is maintained to provide at least 35%, preferably at least 45%, more preferably at least 55% of the air permeability of the dry absorbent article.

The artificial menstrual fluid is described in details herein after. The artificial menstrual fluid in this comparison is entered in the center of the article. Air permeability (that is the capacity of an absorbent structure to exchange/circulate air) is measured in accordance with the air permeability test disclosed herein after.

By selecting chitosan materials and using them in breathable absorbent articles not only improved physical comfort to the user during use is provided but also reduction or even prevention of the formation of malodor as well as increased level of protection are provided. Advantageously it has been found that one single ingredient used in an absorbent breathable article combines the three benefits of improved comfort during use, malodor reduction over a broad range of malodors compounds and leakage/wet through reduction.

Without to be bound by any theory it is believed that chitosan materials provide fluid absorption and odor control of malodorous components associated with bodily fluid by multiple mechanisms.

Firstly, the odor and fluid absorption and retention characteristics of chitosan materials due to the presence in the polymer structure of ionisable cationic functional groups. These groups are usually ammonium groups, a high proportion of which are in the salt form when the polymer is dry but which undergo dissociation and salvation upon contact with bodily fluid. In the dissociated state, the polymer chain will have a series of functional groups attached to it which groups have the same electric charge (e.g., $—NH_3^{+\:+}H_3N—$) and thus repel one another. This leads to expansion of the polymer structure, which, in turn permits absorption of molecules (malodor and fluid).

Secondly, the positively charged cationic groups of the chitosan materials will interact with negatively charged anionic group-bearing molecules present in bodily fluids, like the carboxylic groups of proteins or hydroxylic acid bearing entities like short chain acid (e.g., butyric acid) and thus forms tri-dimensional net which will entrap most molecules (like lipids, acids) thereby retaining fluid and malodor.

Thirdly the chitosan materials are believed to act as antimicrobial agents. Indeed the chitosan material with its positively charged cationic groups will interfere with negatively charged surface of microorganism walls, thereby inhibiting the growth of such microorganisms or even killing such microorganisms. The chitosan material will also interfere with negatively charged surface of enzymes, thereby inactivating the enzymatic activity, which, like the microbial activity, are otherwise responsible for the formation of malodorous components. The chitosan materials further act by their indirect antimicrobial activity by linking some of the microorganism nutriments like lipids and/or minerals, this by their chelating properties.

It is believed that the breathable environment does not only deliver the primary comfort benefit but also contributes to the effective odor prevention benefits associated with the articles according to the present invention. Indeed the breathability of the article, which reduces the hot, humid and anaerobic environment between the skin of the wearer and the surface of the absorbent article, contributes in an overall reduction of growth of microorganisms, thereby reducing the presence of pathogen organisms in the bodily fluid.

The reduction in the hot, humid and occlusive environment between the vicinity of the skin of the wearer and the article itself also reduces the tendency of the wearer to perspire. Consequently, the amount of associated perspiration related odor will be reduced. Thus, the breathability of the article actually reduces the amount of odor generated within the absorbent article.

In a particularly suitable embodiment of the present invention the chitosan material is located in the core of the absorbent article directed towards the backsheet (i.e., in the core but in closer proximity to the backsheet than to the topsheet) or in the backsheet itself (e.g., the secondary backsheet). Such executions allow to best combine the needs of highly breathable absorbent articles and reduction or even prevention of odor and fluid leakage through the breathable backsheet.

Advantageously the use of chitosan material is compatible with skin safety. Indeed, the cationic properties of chitosan materials allow binding to the negatively charged surface of the skin, typically in the case of rewetting occurrence (where chitosan can be brought in contact with the skin trough bodily fluid transport), thereby moisturizing the skin and providing a long lasting softness and fullness.

Also chitosan material has been found to be particularly suitable for absorbent articles like breast pads as an effective material for absorbing lactational fluids. Indeed the use of chitosan material in breast pads/nursing pads provides effective fluid absorption towards lactational fluids, i.e. fluids containing a high proportion of electrolytes and proteins that typically would interfere with usually used gelling absorbent materials like polyacrylates. Also the antimicrobial activity of chitosan material will prevent the formation of skin irritation or even breast infection while being safe to babies. Thus in its broader aspect, the present invention also encompasses nursing pads comprising chitosan material.

BACKGROUND ART OF THE INVENTION

The incorporation of breathable backsheets in absorbent articles for improved wearer comfort has been described in the art such as for example in GB 2 184 389, U.S. Pat. No. 3,881,489 and EP 203 821. EP-A-811 392 discloses breathable absorbent articles having a chelating agent based odor control system.

Articles comprising chitosan materials are known from the art. For example WO99/32697 discloses that chitosan and chitin-based polymers exhibit increased antimicrobial activity when coated onto the surface of a hydrophobic material such as polypropylene.

None of these prior art references suggests the benefit of providing breathable absorbent articles comprising chitosan materials, namely those of providing absorbent articles that combine high breathable performance for comfort even upon loading of the articles together with reduced leakage/ wet through while delivering effective odor control benefit over a broad range of malodors.

BRIEF DESCRIPTION OF THE DRAWINGS

The invention is further described with reference to the accompanying drawings.

SUMMARY OF THE INVENTION

The present invention relates to an absorbent article suitable for absorbing bodily fluid, having a breathable backsheet and comprising a chitosan material.

The present invention also encompasses the use of chitosan material in a breathable absorbent article suitable for absorbing bodily fluid, comprising a liquid permeable topsheet, an absorbent core and a breathable backsheet, for maintaining effective breathability of the article during use.

DETAILED DESCRIPTION OF THE INVENTION

The present invention relates to breathable absorbent articles such as sanitary napkins, panty liners, incontinence devices, nursing pads/breast pads and baby diapers, interlabial pads. Typically such products comprise a liquid pervious topsheet, a backsheet and an absorbent core intermediate the topsheet and the backsheet. According to the present invention the breathability of the absorbent article is provided by the presence of a breathable backsheet which thereby allows the circulation of water vapor and preferably both water vapor and air through it.

Typically the absorbent articles according to the present invention have an air permeability (as measured by the air permeability test method for dry article described herein after) higher than 300 l/m2/s, preferably higher than 600 l/m2/s, and more preferably higher than 900 l/m2/s.

By "bodily fluid" it is meant herein any fluid produced by human or animal body including for instance perspiration, urine, menstrual fluids, faeces, vaginal secretions, lactational fluid and the like.

Chitosan Materials

According to the present invention the articles comprise as an essential component a chitosan material or a mixture thereof.

By 'chitosan material' it is meant herein chitosans, modified chitosans, crosslinked chitosans and chitosan salts.

Chitosan is a partially or fully deacetylated form of chitin, a naturally occurring polysaccharide. Indeed, chitosan is an aminopolysaccharide usually prepared by deacetylation of chitin (poly-beta(1,4)-N-acetyl-D-glucosamine).

Chitin occurs widely in nature, for example, in the cell walls of fungi and the hard shell of insect and crustaceans. The waste from shrimp-, lobster, and crab seafood industries typically contains about 10 to about 15 percent chitin and is a readily available source of supply. In the natural state, chitin generally occurs only in small flakes or short fibrous material, such as from the carapace or tendons of crustaceans. There is generally no source, as with cotton in the cellulosics, that forms useful shaped articles without solution and re-precipitation or re-naturing.

More specifically, chitin is a mucopolysaccharide, poly-N-acetyl-D-glucosamine with the following formula:

wherein x represents the degree of polymerization. Although x cannot be determined precisely, x is believed to be commonly in the range of from about 30 to about 50,000.

Chitosan is not a single, definite chemical entity but varies in composition depending on the conditions of manufacture. It may be equally defined as chitin sufficiently deacetylated to form soluble amine salts. Chitosan is the beta-(1–4) polysaccharide of D-glucosamine, and is structurally similar to cellulose, except that the C-2 hydroxyl group in cellulose is substituted with a primary amine group in chitosan. The large number of free amine groups makes chitosan a polymeric weak base. Solutions of chitosan are generally highly viscous, resembling those of natural gums.

The chitosan used herein is suitably in relatively pure form. Methods for the manufacture of pure chitosan are well known. Generally, chitin is milled into a powder and dematerialized with an organic acid such as acetic acid. Proteins and lipids are then removed by treatment with a base, such as sodium hydroxide, followed by chitin deacetylation by treatment with concentrated base, such as 40 percent sodium hydroxide. The chitosan formed is washed with water until the desired pH is reached.

The properties of chitosan relate to its polyelectrolyte and polymeric carbohydrate character. Thus, it is generally insoluble in water, in alkaline solutions at pH levels above about 6.5, or in organic solvents. It generally dissolves readily in dilute solutions of organic acids such as formic, acetic, tartaric, glycolic, lactic and citric acids, and also in dilute mineral acids, except, for example, sulfuric acid. In general, the amount of acid required to dissolve chitosan is approximately stoichiometric with the amino groups. Since the pKa for the amino groups present in chitosan is between 6.0 and 7.0, they can be protonated in very dilute acids or even close to neutral conditions, rendering a cationic nature to this biopolymer. This cationic nature is the basis of many of the benefits of chitosan. Indeed, chitosan material can be considered as a linear polyelectrolyte with a high charge density which can interact with negatively charged surfaces, like proteins (e.g., by interfering with the proteinic wall construction of microorganisms, thereby acting as an antimicrobial agent and/or by reacting with the proteins present in bodily fluid, like menses, thereby acting as a gelifying agent for such fluid) or like anionic absorbent gelling materials (in the preferred embodiment of the present invention wherein anionic absorbent gelling material are present on top of chitosan, thereby further enhancing the odor control properties of the chitosan materials and providing enhanced fluid absorption properties).

Preferred chitosan materials for use herein have an average degree of deacetylation (D.A.) of more than 75%, preferably from 80% to about 100%, even more preferably from 90% to 100% and most preferably from 95% to about 100%. The degree of deacetylation refers to the percentage of the amine groups that are deacetylated. This characteristic is directly related to the hydrogen bonding existing in this biopolymer, affecting its structure, solubility and ultimately its reactivity. The degree of deacetylation can be determined by titration, dye adsorption, UV-VIS, IR, and NMR spectroscopy.

The degree of deacetylation will influence the cationic properties of chitosan. By increasing the degree of deacetylation the cationic character of chitosan materials will increase and thus their antimicrobial properties, their absorbing ability and gelifying ability.

Suitable chitosan materials to use herein include both water-soluble and water insoluble chitosan. As used herein, a material will be considered to be water-soluble when it substantially dissolves in excess water to form a clear and stable solution, thereby, losing its initially particulate form and becoming essentially molecularly dispersed throughout the water solution. Preferred chitosan materials for use herein are water soluble, i.e., at least 0.5 gram, preferably at least 1 gram and more preferably at least 2 grams of the chitosan materials are soluble in 100 grams of water at 25° C. and one atmosphere. By "solubility" of a given compound it is to be understood herein the amount of said compound solubilised in de-ionized water at 25° C. and one atmosphere in absence of precipitate.

As a general rule, the water-soluble chitosan materials will be free from a substantial degree of crosslinking, as crosslinking tends to render the chitosan materials water insoluble.

Water-soluble chitosan materials as defined herein are preferred as they have the benefit to be more active in terms of odor control towards most of the malodorous compounds present and soluble in the bodily fluid. Indeed such water-soluble chitosan materials have the ability to absorb and/or electrostatically interfere with water-soluble malodorous components like short chain acid (e.g., butyric acid) or low molecular weight alcohol (e.g., ethanol). Also water-soluble chitosan materials have the ability to chelate most of the metals necessary to bacterial growth (e.g., Calcium, Zinc).

Chitosan materials (i.e., chitosan and -chitosan salts, modified chitosans and cross-linked chitosans) may generally have a wide range of molecular weights. Chitosan materials with a wide range of molecular weights are suitable for use in the present invention, typically chitosan materials for use herein have a molecular weight ranging from 1 000 to 10 000 000 grams per gram moles and more preferably from 2 000 to 1 000 000. Molecular weight means weight average molecular weight. Methods for determining the weight average molecular weight of chitosan materials are known to those skilled in the art. Typical methods include for example light scattering, intrinsic viscosity and gel permeation chromatography. It is generally most convenient to express the molecular weight of a chitosan material in terms of its viscosity in a 1.0 weight percent aqueous solution at 25° C. with a Brookfield viscometer. It is common to indirectly measure the viscosity of the chitosan material by measuring the viscosity of a corresponding chitosan salt, such as by using a 1.0 weight percent acetic acid aqueous solution. Chitosan materials suitable for use in the present invention will suitably have a viscosity in a 1.0 weight percent aqueous solution at 25° C. of from about 1 mPa·s (1 centipoise) to about 80,000 mPa·s (80,000 centipoise), more suitably from about 30 mPa·s (30 centipoise) to about 10,000 mPa·s (10,000 centipoise), even more suitably from 50 mPa·s (50 centipoise) to about 1,000 mPa·s (1,000 centipoise) and most suitably from 100 mPa·s (100 centipoise) to about 500 mPa·s (500 centipoise).

Chitosan materials pH depends on the preparation of the chitosan materials. Preferred chitosan materials for use herein have an acidic pH, typically in the range of 4 to 6, more preferably from 4 to 5.5 and even more preferably from 4.5 to 5.5. Highly preferred pH is around pH 5, which corresponds to the skin pH. By 'pH of chitosan material' it is meant herein the pH of a 1% chitosan solution (1 gram of chitosan material dissolved in 100 grams of distilled water) measured by pH-meter.

Chitosan materials with acidic pH are preferred herein as the cationic character of acidic chitosan materials will be increased and thus their antimicrobial properties, odor and fluid absorbing ability and gelifying ability. However too high acidity is detrimental to skin safety. Thus it is highly preferred herein to use chitosan materials with a pH in the range of 4.5 to 5.5, thereby delivering the best compromise between odor control and fluid handling properties on one side and skin compatibility on the other side.

Particularly suitable chitosan materials for use herein are chitosan salts, especially water-soluble chitosan salts. A variety of acids can be used for forming chitosan salts. Suitable acids for use are soluble in water or partially soluble in water, are sufficiently acidic to form the ammonium salt of chitosan and yet not sufficiently acidic to cause hydrolysis of chitosan, and are present in amount sufficient to protonate the reactive sites of chitosan.

Preferred acids can be represented by the formula:

R—(COOH)$_n$ wherein n has a value of 1 or 2 or 3 and R represents a mono- or divalent organic radical composed of carbon, hydrogen and optionally at least one of oxygen, nitrogen and sulfur or R is simply a hydroxyl group. Preferred acids are the mono- and dicarboxylic acids composed of carbon, hydrogen, oxygen and nitrogen (also called herein after amino acids). Such acids are highly desired herein as they are biologically acceptable for use against or in proximity to the human body. Illustrative acids, in addition to those previously mentioned include, among others, citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, 2-pyrrolidone-5-carboylic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid and thioglycolic acid. Any chitosan salts formed from the reaction of chitosan with any of these acids are suitable for use herein.

Examples of chitosan salts formed with an inorganic acid include, but are not limited to, chitosan hydrochloride, chitosan hydrobromide, chitosan phosphate, chitosan sulphonate, chitosan chlorosulphonate, chitosan chloroacetate and mixtures thereof. Examples of chitosan salts formed with an organic acid include, but are not limited to, chitosan formate, chitosan acetate, chitosan lactate, chitosan glycolate, chitosan malonate, chitosan epoxysuccinate, chitosan benzoate, chitosan adipate, chitosan citrate, chitosan salicylate, chitosan propionate, chitosan nitrilotriacetate, chitosan itaconate, chitosan hydroxyacetate, chitosan butyrate, chitosan isobutyrate, chitosan acrylate, and mixtures thereof. It is also suitable to form a chitosan salt using a mixture of acids including, for example, both inorganic and organic acids.

Highly preferred chitosan salts for use herein are those formed by the reaction of chitosan with an amino acid. Amino acids are molecules containing both an acidic and amino functional group. The use of amino acids instead of other acids is highly preferred as those chitosan amino salts have higher skin compatibility. Indeed most of the amino acids are naturally present on the skin. Chitosan salts of pyrrolidone carboxylic acid are effective moisturizing agents and are non-irritating to skin.

Amino acids for use herein include both linear and/or cyclo amino acids. Examples of amino acids for use herein include, but are not limited to, alanine, valine, leucine, isoleucine, prolinephenylalanine, triptofane, metionine, glycine, serine, cysteine, tyrosine, asparagine, glutamine, aspartic acid, glutamic acid, lysine, arginine, istydine, hydroxyproline and the like. A particularly suitable example of cyclo amino acid is pyrrolidone carboxylic acid, which is a carboxylic acid of pyrrolidin-2-one as per following formula:

Highly preferred chitosan salts are chitosan pyroglutamate salt, which is a mixture of chitosan (a macromolecule) and pyroglutamic acid (independent monomers), chitosonium pyrrolidone carboxylate, which is the chitosan salt of 2-pyrrolidone-5-carboxylic acid.

Reference is made to WO98/07618, which describes in details processes for the preparation of such chitosan salts.

Other chitosan materials suitable for use herein include cross-linked chitosans and modified chitosans.

Crosslinking agents suitable for use in the present invention are generally water-soluble and do not substantially reduce the antimicrobial properties of chitosan. One suitable crosslinking agent is an organic compound having at least two functional groups or functionalities capable of reacting with active groups located on the chitosan materials. Examples of such active groups include, but are not limited to, carboxylic acid (—COOH), amino (—NH$_2$), or hydroxyl (—OH) groups. Examples of such suitable crosslinking agents include, but are not limited to, diamines, polyamines, diols, polyols, polycarboxylic acids, polyoxides and the like. One way to introduce a crosslinking agent with the chitosan solution is to mix the crosslinking agent with chitosan during preparation of the solution. Another suitable crosslinking agent comprises a metal ion with more than two positive charges, such as $Al^{3+}$, $Fe^{3+}$, $Ce^{3+}$, $Ce^{4+}$, $Ti^{4+}$, $Zr^{4+}$, and $Cr^{3+}$. Since the cations on chitosan possess antimicrobial properties, it is preferred herein to not use a crosslinking agent reacting to the cations, unless no alternative crosslinking agent is available.

In the embodiment herein where crosslinking agents are used, a suitable amount of crosslinking agent is from 0.001 to 30 weight percent based on the total dry weight of chitosan used to prepare the crosslinked-chitosan, more specifically from 0.02 to 20 weight percent, more specifically from 0.05 to 10 weight percent and most preferably from 0.1 to 5 weight percent.

Modified chitosans for use herein are any chitosan where the glucan chains carry pendant groups. Examples of such modified chitosans include carboxymethyl chitosan, methyl pyrrolidinone chitosan, glycol chitosan and the like. Methyl pyrrolidone chitosan is for instance described in U.S. Pat. No. 5,378,472, incorporated herein by reference. Water-soluble glycol chitosan and carboxymethyl chitosan are for instance described in WO87/07618, incorporated herein by reference Particularly suitable modified chitosans for use herein include water-soluble covalently bonded chitosan derivatives or ionically bonded chitosan derivatives obtained by contacting salt of chitosan with electrophilic organic reagents. Such water-soluble chitosan derivatives are described in EP-A737 692, which is herein incorporated by reference.

Suitable electrophilic organic reagents suitable for use for the preparation of chitosan derivatives contain from 2 to 18 carbon atoms or more per molecule and typically from 2 to 10 carbon atoms per molecule. In addition the electrophilic organic reagents contain groups, which are reactive, i.e. capable of forming a covalent bond with a nucleophile. Typical electrophilic organic reagents include, for example, ethylene oxide, propylene oxide, butylene oxide, glycidol, 3-chloro-1,2-propanediol, methyl chloride, ethyl chloride, isatoic anhydride, succinic anhydride, octenylsuccinic anhydride, acetic anhydride, gamma-butyrolactone, b-propiolactone, 1,3-propanesultone, acrylamide, glycidyltrimethyl ammonium chloride, glycidyldimethyl alkylammonium chloride such as lauryl, sodium chlorosulfonate, dimethyl sulfate, sodium chloroethanesulfonate, monochloroacetic acid, alkyl phenyl glycidyl ethers, glycidyl trimethoxysilanes, 1,2-epoxy dodecane. One preferred class of electrophilic organic reagent includes those electrophilic organic reagents, which contain an epoxide group, at least one acid group, preferably a diacid group and have from 3 to 18, preferably from 3 to 6 carbon atoms per molecule. Other preferred electrophilic organic reagents include cis-electrophilic organic reagents and trans-electrophilic organic reagent, with cis-electrophilic organic reagents being especially preferred. The electrophilic organic reagent may react with either the free amine or the underivatized hydroxyl groups of the chitosan. It is known that the amine functionality of the chitosan is generally regarded as a stronger nucleophilic site than the hydroxyl groups. Consequently weaker electrophiles will tend to react more readily with the amine groups than with the hydroxyl groups of the chitosan.

Preferably an effective amount of electrophilic organic reagent is substituted onto the chitosan to achieve the desired properties of the chitosan derivative, namely its water-soluble properties. Typically the chitosan derivatives suitable for use herein (modified chitosan) have a MS of from 0.03 to 10 moles of the electrophilic organic reagent per mole of glucosamine monomer unit. The term molar substitution (MS), means the moles of electrophilic organic reagent substituted on the chitosan per mole of glucosamine monomer unit.

In addition further modified chitosan can be prepared which contain other substituent groups, such as hydroxalkyl ether group (e.g., hydroxyethyl or hydroxypropyl ether groups), carboxyalkyl ether groups (e.g., carboxymethyl group), amide groups (e.g., succinyl groups), ester groups (e.g., acetate groups) or amino groups (e.g., 3-(trimethylammonium chloride)-2-hydroxylpropyl or 3-(dimethyloctadecylammonium chloride)-2-hydroxpropyl ether groups) in addition to the electrophilic organic reagent groups. These other substituent groups may be introduced prior to or subsequent to the reaction with the electrophilic organic reagent, or introduced simultaneously by reaction of the chitosan salt with the electrophilic organic reagent and the other derivatizing reagent.

Typically such covalently bonded chitosan derivative might be obtainable by a process which includes the step of (a) dispersing a salt of chitosan (e.g., any one of those described herein before) in an effective amount of an aqueous caustic medium to form a neutralized chitosan containing free amine groups, (b) introducing an electrophilic organic reagent in the slurry and (c) maintaining the slurry at a temperature and time effective to promote the substitution of the electrophilic organic reagent onto the chitosan to form a covalently bonded chitosan derivative and the dissolution of the covalently bonded chitosan into the aqueous medium. The chitosan derivatives can be prepared in either salt form, i.e., ionically bonded, or in the covalently bonded from. Processes for the preparation of such chitosan derivatives are described in depth in EP-A-737 692, incorporated herein by reference.

Suitable chitosans are commercially available from numerous vendors. Exemplary of a commercially available chitosan materials are those available from for example the Vanson Company. The preferred chitosan salt for use herein is chitosan pyrrolidone carboxylate (also called chitosonium pyrrolidone carboxylate), which has a degree of deacetylation of more than 85%, a water solubility of 1% (1 gram is soluble in 100 grams of distilled water at 25° C. and one atmosphere), a pH of 4.5 and a viscosity between 100–300 cps. Chitosan pyrrolidone carboxylate is commercially available under the name Kytamer® PC from Amerchol Corporation.

Typically, the articles like disposable absorbent articles comprise chitosan material or a mixture thereof at a level of from 0.5 gm$^{-2}$ to 500 gm$^{-2}$, preferably from 1 to 200 gm$^{-2}$, more preferably from 3 gm$^{-2}$ to 100 gm$^{-2}$ and most preferably from 4 gm$^{-2}$ to 50 gm$^{-2}$.

The present invention is based on the finding that the presence of a chitosan material (preferably a chitosan salt like chitosonium pyrrolidone carboxylate), in a breathable absorbent article provides not only initial comfort but maintain a higher level of comfort during use as well as effective odor control towards malodors associated with bodily fluids, while providing at the same time high level of protection.

Chitosan materials have the ability of instantaneously changing the physical properties of bodily fluids. Indeed a gelification of the bodily fluid is obtained when the fluid comes into contact with chitosan material. Chitosan material has the advantage of having a high gelification rate. This can be quantified by measuring the quantity and speed of wicking within the material. It is important to consider both the speed of transport and the quantity transported such that a value for the liquid transport would indicate quantity of liquid transported per time increment through a defined cross-section of the material. This can be measured for example against gravitational forces or for horizontal wicking.

The present invention is based on the finding that the use of chitosan material (especially chitosan salts as described herein before) in a breathable absorbent article allows to maintain an effective level of breathability, especially air transmission ability, during use (i.e., upon loading of the article by bodily fluid) while at the same time reducing leakage/wet through of the breathable absorbent article and delivering enhanced odor control.

Optional Agents

The articles according to the present invention may further comprise on top of the chitosan materials described herein before, other conventional agents or mixtures thereof.

Optional Absorbent Gelling Materials

According to the present invention the articles comprise as an optional component an absorbent gelling material (sometimes referred to as "super-sorber").

Particularly preferred absorbent gelling materials for use herein are anionic absorbent gelling materials, i.e., absorbent gelling materials, which are predominantly negatively charged. These absorbent gelling materials can be any material having superabsorbent properties in which the functional groups are anionic, namely sulphonic groups, sulphate groups, phosphate groups or carboxyl groups. Preferably the functional groups are carboxyl groups. Particularly preferred anionic absorbent gelling materials for use herein are synthetic anionic absorbent gelling materials. Synthetic anionic absorbent gelling materials are preferred herein as they deliver higher odor and fluid absorption performance, this even under pressure, as compared to the absorption performance associated with natural anionic absorbent gelling materials like anionic polysaccharides.

Generally the functional groups are attached to a slightly cross-linked acrylic base polymer. For example the base polymer may be a polyacrylamide, polyvinyl alcohol, ethylene maleic anhydride copolymer, polyvinylether, polyvinyl sulphonic acid, polyacrylic acid, polyvinylpyrrolidone and polyvinylmorpholine. Copolymers of these monomers can also be used. Particular base polymers include cross-linked polyacrylates, hydrolyzed acrylonitrile grafted starch, starch polyacrylates and isobutylene maleic anhydride copolymers.

Such materials form hydrogels on contact with water (e.g., with urine, blood, and the like). One highly preferred type of hydrogel-forming, absorbent gelling material is based on polyacids, especially polyacrylic acid. Hydrogel-forming polymeric materials of this type are those, which, upon contact with fluids (i.e., liquids) such as water or body fluids, imbibe such fluids and thereby form hydrogels. These preferred absorbent gelling materials will generally comprise substantially water-insoluble, slightly cross-linked, partially neutralized, hydrogel-forming polymer materials prepared from polymerisable, unsaturated, acid-containing monomers. In such materials, the polymeric component formed from unsaturated, acid-containing monomers may comprise the entire gelling agent or may be grafted onto other types of polymer moieties such as starch or cellulose. Acrylic acid grafted starch materials are of this latter type. Thus, the preferred absorbent gelling materials include hydrolyzed acrylonitrile grafted starch, acrylic acid grafted starch, polyacrylates, maleic anhydride-based copolymers and combinations thereof. Especially preferred absorbent gelling materials are the polyacrylates and acrylic acid grafted starch.

Whatever the nature of the polymer components of the preferred absorbent gelling materials, such materials will in general be slightly cross-linked. Crosslinking serves to render these preferred hydrogel-forming absorbent materials substantially water-insoluble, and cross-linking also in part determines the gel volume and extractable polymer characteristics of the hydrogels formed there from. Suitable cross-linking agents are well known in the art and include, for example, (1) compounds having at least two polymerisable double bonds; (2) compounds having at least one polymerisable double bond and at least one functional group reactive with the acid-containing monomer material; (3) compounds having at least two functional groups reactive with the acid-containing monomer materials; and (4) polyvalent metal compounds which can from ionic cross-linkages. Cross-linking agents of the foregoing types are described in greater detail in Masuda et al; U.S. Pat. No. 4,076,663; Issued Feb. 28, 1978. Preferred cross-linking agents are the di- or polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred materials. More preferably, the cross-linking agent will comprise from about 0.01 mole percent to 3 mole percent of the gelling materials used herein.

The preferred absorbent gelling materials used herein are those which have a relatively high capacity for imbibing fluids encountered in the absorbent articles; this capacity can be quantified by referencing the "gel volume" of said absorbent gelling materials. Gel volume can be defined in terms of the amount of synthetic urine absorbed by any given absorbent gelling agent buffer and is specified as grams of synthetic urine per gram of gelling agent.

Gel volume in synthetic urine (see Brandt, et al, below) can be determined by forming a suspension of about 0.1–0.2 parts of dried absorbent gelling material to be tested with about 20 parts of synthetic urine. This suspension is maintained at ambient temperature under gentle stirring for about 1 hour so that swelling equilibrium is attained. The gel volume (grams of synthetic urine per gram of absorbent gelling material) is then calculated from the weight fraction of the gelling agent in the suspension and the ratio of the liquid volume excluded from the formed hydrogel to the total volume of the suspension. The preferred absorbent gelling materials useful in this invention will have a gel volume of from about 20 to 70 grams, more preferably from about 30 to 60 grams, of synthetic urine per gram of absorbent gelling material.

Another feature of the most highly preferred absorbent gelling materials relates to the level of extractable polymer material present in said materials. Extractable polymer levels can be determined by contacting a sample of preferred absorbent gelling material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issues Mar. 31, 1987, U.S. Pat. No. Reissue 32,649, The absorbent gelling materials which are especially useful in the absorbent articles herein are those which have an equilibrium extractable content in synthetic urine of no more than about 17%, preferably no more than about 10% by weight of the absorbent gelling material.

The preferred, slightly cross-linked, hydrogel-forming absorbent gelling materials will generally be employed in their partially neutralized form. For purposes described herein, such materials are considered partially neutralized when at least 25 mole percent, and preferably at least 50 mole percent of monomers used to form the polymer are acid group-containing monomers, which have been neutralized with a salt-forming cation. Suitable salt-forming cations include alkali metal, ammonium, substituted ammonium and amines. This percentage of the total monomers utilized, which are neutralized acid group-containing monomers, is referred to as the "degree of neutralization". Typically, commercial absorbent gelling materials have a degree of neutralization somewhat from 25% to 90%.

The absorbent gelling materials herein before described are typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

The size of the absorbent gelling material particles may vary over a wide range. For reason of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use herein are absorbent gelling material particles substantially all of which have a particle size of from about 30 microns to about 2 mm. "Particle Size" as used herein means the weighted average of the smallest dimension of the individual particles.

The amount of absorbent gelling material particles used in the article according to the present invention, especially disposable absorbent articles, will typically range from 5 $gm^{-2}$ to 250 $gm^{-2}$, preferably from 7 $gm^{-2}$ to 150 $gm^{-2}$, more preferably from 10 $gm^{-2}$ to 100 $gm^{-2}$.

An anionic absorbent gelling material is suitably used on top of the chitosan material herein as it is able to further enhance the advantages of the present invention. Indeed anionic absorbent gelling materials are believed to further enhance the cationic properties of chitosan materials. Without to be bound by any theory, it is believed that the negatively charged anionic groups of anionic absorbent gelling materials protonate the cationic groups of chitosan materials, thereby enhancing their cationic properties. This translates in improved gelification properties, especially further enhanced gelification rate. Thus the addition of such anionic absorbent gelling material further contributes in maintaining effective breathability of the article during loading of bodily fluid. The enhanced cationic properties of the chitosan materials further translate in improved odor control properties too.

Advantageously combining anionic absorbent gelling materials, namely synthetic anionic absorbent gelling materials as described herein (typically having a degree of neutralization of from 25% to 90%) together with chitosan materials, in an absorbent article results in outstanding fluid absorption capacity not only towards water but especially towards electrolytes-containing solutions like menses. This is believed to be due to the reduction of the salt poisoning effect associated to the presence of chitosan materials beside anionic absorbent gelling material.

Furthermore the use of anionic absorbent gelling materials, namely synthetic anionic absorbent gelling materials as described herein (typically having a degree of neutralization of from 25% to 90%) on top of chitosan materials, in an absorbent article, exhibits high gel strength during fluid absorption. Indeed this combination results in improved absorption capacity under load conditions, in decreased rewetting and wetting through.

In a preferred embodiment according to the present invention chitosan material and the anionic absorbent gelling material are present in the absorbent article at a weight ratio of chitosan material to absorbent gelling material of from 10:1 to 1:10, preferably from 5:1 to 1:5, more preferably from 3:1 to 1:3 and most preferably from 2:1 to 1:2. Within these ratio ranges optimum performance on fluid handling, odor control and breathability upon loading of the articles are obtained.

Optional Additional Odor Control Agents

Additional odor control agent or combinations thereof, known in the art for this purpose may be used herein. These agents can typically be classified according to the type of odor the agent is intended to combat. Odors may be chemically classified as being acidic, basic or neutral.

Alternatively, the odor control agents may be categorized with respect to the mechanism by which the malodor detection is reduced or prevented. For example, odor control agents which chemically react with malodorous compounds or with compounds which produce malodorous degradation products thereby generating compounds lacking odor or having an odor acceptable to consumers may also be utilized herein.

Suitable odor control agents for use herein typically include carboxylic acids such as citric acid, lauric acid, boric acid, adipic acid and maleic acid, activated carbons, clays, zeolites, silicas, diatomaceous earth and starches. Such odor control agents and systems are disclosed in more details hereinafter and for example in EP-A-348 978, EP-A-510 619, WO 91/12029, WO91/11977, WO 91/12030, WO 81/01643 and WO 96/06589. Highly preferred odor control agents are zeolite together with silicate.

In a preferred embodiment herein the absorbent article comprises as the additional odor control agents zeolite together with silica in a weight ratio of silica to zeolite of from 1:5 to 5:1, preferably from 3:1 to 1:3 and most preferably about 1:1. This combination has been found to be particularly effective in terms of odor control over a broad range of malodorous compounds. Silicate and zeolite have a complementary odor control properties towards various malodorous compounds, thereby resulting in further improved overall odor control reduction.

Alternative odor control agents are ion exchange resins such as those described in U.S. Pat. Nos. 4,289,513 and 3,340,875.

Masking agents such as perfumes may also be used as odor control agents herein.

Suitable odor control agents also include chelating agents and may be selected from amino carboxylates such as for example ethylenediamine-tetracetate, as described for example in U.S. Pat. No. 4,356,190, amino phosphonates such as ethylenediaminetetrakis (methylene-phosphonates), polyfunctionally-substituted aromatic chelating agents as described in U.S. Pat. No. 3,812,044 and mixtures thereof. Without intending to be bound by theory it is believed that the benefit of these materials is in part due to their exceptional ability to remove iron, copper, calcium, magnesium and manganese ions present in the absorbed fluids and their degradation products by the formation of chelates.

Another suitable odor control agent for use herein is an acidic pH buffer system, such as citric acid and sodium bicarbonate, sodium phosphate and sorbic acid buffer systems. Such acidic pH buffer system will contribute to the benefits of the present invention by further enhancing and maintaining the cationic properties of the chitosan materials herein, even upon aging of the bodily fluid, i.e., upon prolonged wearing time of an article by the user.

Typically, the articles herein may comprise the additional odor control agent or a mixture thereof at a level of from 0 $gm^{-2}$ to 600 $gm^{-2}$, preferably from 5 to 500 $gm^{-2}$, more preferably from 10 $gm^{-2}$ to 350 $gm^{-2}$ and most preferably from 20 $gm^{-2}$ to 200 $gm^{-2}$.

The Disposable Articles

Preferred breathable articles herein are pantiliners, feminine napkins, incontinent pads, diapers, nursing pads, and the like. The chitosan material (and optional absorbent gelling material and/or optional additional odor control agent(s)) may be incorporated into such articles by any of the methods known for such purpose by those skilled in the art.

The articles of the invention may comprise chitosan materials, typically chitosan material powder, coated chitosan material or any other form of chitosan material, in any location of such articles. Typically chitosan materials may be distributed homogeneously or non-homogeneously in at least one or several layers of the topsheet and/or in at least one or several layers of the backsheet and/or in at least one or several layers of the core. Also chitosan materials may be distributed homogeneously or non homogeneously on the whole surface of the desired layer or layers, or on one or several area of the surface layer/layers to which they are applied to (e.g. central area and/or surrounding area like the edges of a layer of the absorbent article) or mixtures thereof.

Chitosan material may typically be present in the absorbent core of the absorbent article (also called intermediate layer which is positioned between the topsheet and the backsheet of the absorbent article). More preferably chitosan material may be present in the fluid storage layer as described herein. The presence of the chitosan material in the core is suitable as the core collects and absorbs bodily fluids. In a preferred embodiment of the present invention the chitosan material and optional additional agents are typically incorporated between two layers of cellulose tissue, typically two layers of air laid tissue. Optionally the system may be bonded between the two cellulose tissue layers (laminate) with, for example, a hot melt adhesive (e.g., polyethylene powder) or any suitable bonding system like for instance glue (e.g., those commercially available from ATO Findley under the name H20-31®). Advantageously the use of conventional glue allows to avoid the heating step necessary when using polyethylene powder. Adhesive lines are preferably also placed on the edges of the laminate to ensure that the edges of the laminate stick and any loose chitosan materials and optional additional agents present do not fall out of the laminate.

In particular embodiments of the present invention chitosan material is present in the absorbent core but directed towards the backsheet. By 'directed towards the backsheet' it is meant that the chitosan material is closer to the backsheet than the topsheet. This can be achieved where the absorbent core comprises laminate by disposing chitosan material on either sides or both sides of the air laid cellulose layer of the laminate, which is facing the backsheet. Typically the chitosan material might be coated or sprayed onto such an air laid layer. Or a chitosan film/layer might be used as suitable layers to form such a laminate. This can be achieved too by disposing chitosan material particle/powder so as to form a gradient concentration through the thickness of the absorbent core, a so called Z-directional gradient, wherein the concentration of the chitosan material increases from the surface of the absorbent core facing the topsheet to the surface of the absorbent core facing the backsheet. Combinations of such constructions are also included herein. In other embodiments of the present invention the chitosan material is located in the backsheet itself (preferably the first layer of the backsheet as defined herein after, also called secondary backsheet, i.e., the layer in contact with the absorbent core). All these executions are particularly suitable as they provide effective breathability during use, effective fluid handling properties as well as effective odor control properties. Indeed effective leakage/wet through prevention as well as odor control are provided by retaining the fluid either in the core but in closer proximity towards the backsheet than the topsheet or in the backsheet itself.

In the preferred embodiment of the present invention, wherein an absorbent gelling material, typically a synthetic anionic absorbent gelling material, is present in the absorbent article, the absorbent gelling material is positioned such that at least a portion of the bodily fluid comes into contact with said absorbent gelling material before contacting the chitosan material. Such executions are particularly beneficial for combining optimum breathability during use, optimum odor control properties and optimum fluid handling, i.e., optimum fluid absorption and retention without any leakage through or rewetting occurrence. Without to be bound by any theory, it is speculated that the odor control properties are supported by the fact that the major portion of the bodily fluid contacts the absorbent gelling material first and is retained in close proximity to the absorbing gelling material, thereby reducing the wetting of the chitosan material and thus enhancing its odor control ability. Also the first contact of the fluid by the absorbent gelling material (which has the properties of acidifying the bodily fluid) allows to keep the pH of the absorbed fluid stable at nearly neutral value or even to acidify it slightly thereby reducing the formation of alkaline odorous compounds but also maintaining or even enhancing the cationic properties of the chitosan materials and thus their antimicrobial properties but also their gelification properties. It is further speculated that the chitosan material due to its gelifying properties will have the tendency to retain the fluids and odor having by passed the absorbent gelling material, thereby reducing or even preventing any fluid and odor leakage through the backsheet. In other words the presence of absorbent gelling material located so that the fluid first contact it before contacting the chitosan material provides further improved odor control and fluid control as well as helps in maintaining even more effective breathability during use.

Advantageously the present invention also encompasses absorbent articles suitable for absorbing bodily fluid, comprising a liquid permeable topsheet, a breathable backsheet and an absorbent core, the article comprising an absorbent gelling material on top of the chitosan material, these materials being located in the absorbent articles such that the bodily fluid first contacts the absorbing gelling material before contacting the chitosan material. This is typically achieved in execution wherein the chitosan material is located beneath the absorbent gelling material (in a vertical superimposed relationship) and/or wherein the absorbent gelling material is placed nearest the liquid receiving region (so called wetting location, typically found in the center of the absorbent article) and the chitosan material is placed in a separate region outside said wetting location for instance in a region surrounding said wetting region.

In the preferred absorbent articles of the present invention the absorbent gelling material is located towards the topsheet whereas the chitosan material is located towards the backsheet, i.e., the chitosan material is further away from the topsheet than the absorbent gelling material. Preferably the absorbent gelling material is located in the core and the chitosan material is located further away from the topsheet than the absorbent gelling material. For example when a laminate of two fibrous layers is used as the absorbent core, chitosan material is typically the fibrous layer directed towards the backsheet (by using it per se as a film layer or by coating or spraying it onto either sides of the layers or even both sides) and the absorbent gelling material is located between the two layers of the laminate (i.e., the one directed to the topsheet and the one directed to the backsheet). Also chitosan material particles and the absorbent gelling material particles might be incorporated in reverse gradient concentration through the thickness of the absorbent core. This can be achieved by disposing chitosan material particle so as to form a gradient concentration through the thickness of the absorbent core, a so called Z-directional gradient, wherein the concentration of the chitosan materials increases from the surface of the absorbent core facing the topsheet to the surface of the absorbent core and by disposing the gelling absorbent material particles so as to form a gradient concentration through the thickness of the absorbent core, wherein the concentration of the absorbent gelling materials decreases from the surface of the absorbent core facing the topsheet to the surface of the absorbent core facing the backsheet.

In other embodiments of the present invention, the absorbent gelling material is physically separated from the chitosan material, typically by being located in a separate layer from the chitosan material. Both materials might be present in the absorbent core but separated by a layer. Alternatively the absorbent article may comprise the absorbent gelling material in the core and the chitosan material in/on the backsheet, typically the secondary backsheet.

The chitosan materials as described herein may be incorporated in particle form as a powder or a granulate. When used in particle form the chitosan materials as described herein and the optional absorbent gelling material and optional odor control agent may be granulated separately and then mixed together or granulated together.

The chitosan material might also be applied onto the desired layer by simply spraying a solution containing chitosan material and letting said layer to dry. This is an easy and cost effective way to introduce chitosan material onto for example a cellulose air laid tissue before the lamination process and thus before the manufacturing process of the articles.

Suitable breathable absorbent article according to the present invention include those described as follows:

Backsheet

According to the present invention, the absorbent articles comprise as an essential component a breathable backsheet. The primary role of the breathable backsheet is to prevent the extrudes absorbed and contained in the absorbent article from wetting articles that contact the absorbent article such as pyjamas and undergarments. In order to achieve this, the backsheet typically extends across the whole of the absorbent structure and may extend into and form part of or all of side flaps, side wrapping elements or wings. In addition to the prevention of liquid transport through the backsheet however, the breathable backsheet also permits the transfer of water vapor and preferably both water vapor and air through it and thus allows the circulation of air into and out of the backsheet and the absorbent article itself.

Suitable breathable backsheets for use herein include all breathable backsheets known in the art. In principle there are two types of breathable backsheets, single layer breathable backsheets, which are breathable and impervious to liquids and backsheets having at least two layers, which in combination provide both breathability and liquid imperviousness.

Suitable single layer breathable backsheets for use herein include those described for example in GB A 2184 389, GB A 2184 390, GB A 2184 391, U.S. Pat. No. 4,591,523, U.S. Pat. No. 3,989,867 U.S. Pat. No. 3,156,242 and European Patent Application number 95120653.1.

Suitable dual or multi layer breathable backsheets for use herein include those exemplified in U.S. Pat. No. 3,881,489, U.S. Pat. No. 4,341,216, U.S. Pat. No. 4,713,068, U.S. Pat. No. 4,818,600, EPO 203 821, EPO 710 471, EPO 710 472, European Patent Application numbers 95120647.3, 95120652.3, 95120653.1 and 96830097.0.

Particularly preferred are backsheets meeting the requirements as defined in European Patent Application number 96830343.8 and more preferably wherein the absorbent article also meets the requirements as described therein.

According to the present invention the breathable backsheet comprises at least one, preferably at least two water vapor permeable layers. Suitable water vapor permeable layers include 2 dimensional, planar micro and macroporous films, monolithic films, macroscopically expanded films and formed apertured films. According to the present invention the apertures in said layer may be of any configuration, but are preferably spherical or oblong. The apertures may also be of varying dimensions. In a preferred embodiment the apertures are preferably evenly distributed across the entire surface of the layer, however layers having only certain regions of the surface having apertures are also envisioned.

2 dimensional planar films as used herein have apertures having an average diameter of from 5 micrometers to 200 micrometers. Typically, 2-dimensional planar micro porous films suitable for use herein have apertures having average diameters of from 150 micrometers to 5 micrometers, preferably from 120 micrometers to 10 micrometers, most preferably from 90 micrometers to 15 micrometers. Typical 2 dimensional planar macroporous films have apertures having average diameters of from 200 micrometers to 90 micrometers. Macroscopically expanded films and formed apertured films suitable for use herein typically have apertures having diameters from 100 micrometers to 500 micrometers. Embodiments according to the present invention wherein the backsheet comprises a macroscopically expanded film or an apertured formed film, the backsheet will typically have an open area of more than 5%, preferably from 10% to 35% of the total backsheet surface area.

Suitable 2 dimensional planar layers of the backsheet may be made of any material known in the art, but are preferably manufactured from commonly available polymeric materials. Suitable materials are for example GORE-TEX™ or Sympatex™ type materials well known in the art for their application in so-called breathable clothing. Other suitable materials include XMP-1001 of Minnesota Mining and Manufacturing Company, St. Paul, Minn., USA. As used herein the term 2 dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein. In addition, the dimensions of the apertures produced by this method may be increased by applying a force across the plane of the backsheet layer (i.e. stretching the layer).

Suitable apertured formed films include films, which have discrete apertures, which extend beyond the horizontal plane of the garment-facing surface of the layer towards the core thereby forming protuberances. The protuberances have an orifice located at their terminating ends. Preferably said protuberances are of a funnel shape, similar to those described in U.S. Pat. No. 3,929,135. The apertures located within the plane and the orifices located at the terminating end of protuberance themselves maybe circular or non circular, provided the cross sectional dimension or area of the orifice at the termination of the protuberance is smaller than the cross sectional dimension or area of the aperture located within the garment facing surface of the layer. Preferably said apertured preformed films are uni-directional such that they have at least substantially, if not complete one directional fluid transport towards the core. Suitable macroscopically expanded films for use herein include films as described in for example in U.S. Pat. No. 637,819 and U.S. Pat. No. 4,591,523.

Suitable macroscopically expanded films for use herein include films as described in for example U.S. Pat. No. 4,637,819 and U.S. Pat. No. 4,591,523.

Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours International S.A., Switzerland.

According to the present invention the backsheet may comprise in addition to said water vapor permeable layer additional backsheet layers. Said additional layers may be located on either side of said water vapor permeable layer of the backsheet. The additional layers may be of any material, such as fibrous layers or additional water vapor permeable layers as described herein above.

In a particularly preferred embodiment herein a dual or multiple layer breathable backsheet composite is used in the absorbent article. According to the present invention suitable breathable backsheets for use herein comprise at least a first and a second layer. The first layer is positioned between the garment-facing surface of the absorbent core and the wearer-facing surface of the second layer. It is oriented such that it retards or prevents liquid from passing from the absorbent core towards the outside while allowing free airflow and water vapor through it. The second layer provides water vapor and air permeability so as to support breathability of the article. In addition to water vapor permeability the air permeability is desirable in order to further improve the comfort benefit from the breathability of the article.

Such a first layer is preferably in direct contact with the absorbent core. It provides air and water vapor permeability by being apertured. Preferably this layer is made in accordance with the aforementioned U.S. Pat. No. 5,591,510 or PCT WO-97/03818, WO-97/03795. In particular, this layer comprises a polymeric film having capillaries. The capillaries extend away from the wearer-facing surface of film at an angle, which is less then 90 degrees. Preferably the capillaries are evenly distributed across the entire surface of the layer, and are all identical. However, layers having only certain regions of the surface provided with apertures, for example only an area outside the region aligned with the central loading zone of the absorbent core, maybe provided with such capillaries.

Methods for making such three-dimensional polymeric films with capillary apertures are identical or similar to those found in the apertured film topsheet references, the apertured formed film references and the micro-/macroscopically expended film references cited above. Typically a polymeric film such as a polyethylene (LDPE, LLDPE, MDPE, HDPE or laminates thereof) or preferably a monolithic polymeric film is heated close to its melting point and exposed through a forming screen to a suction force which pulls those areas exposed to the force into the forming apertures which are shaped such that the film is formed into that shape and, when the suction force is high enough, the film breaks at its end thereby forming an aperture through the film.

Especially using a monolithic polymer film as the material for the first layer provides water vapor permeability even under stress conditions. While the apertures provide air permeability during "leakage safe" situations but close the capillaries under stress conditions the monolithic material maintains water vapor permeability in such a case. Preferred breathable monolithic film materials for use herein are those having a high vapor exchange. Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours international S.A, Switzerland.

Various forms, shapes, sizes and configurations of the capillaries are disclosed in EP-A-934735 and EP-A-934736 both of which are herein incorporated for reference. In particular the apertures form capillaries, which have sidewalls. The capillaries extend away from the wearer-facing surface of the film for a length, which typically should be at least in the order of magnitude of the largest diameter of the aperture while this distance can reach up to several times the largest aperture diameter. The capillaries have a first opening in the plane of the garment-facing surface of the film and a second opening, which is the opening, formed when the suction force (such as a vacuum) in the above mentioned process creates the aperture. Naturally the edge of the second opening may be rugged or uneven, comprising loose elements extending from the edge of the opening. However, it is preferred that the opening be as smooth as possible so as not to create a liquid transport entanglement between the extending elements at the end of the second opening of the capillary with the absorbent core in the absorbent article (in contrast this may be desirable for apertured film topsheets where such loose elements provide the function of sucker feet). The capillaries in the first layer of the breathable backsheet allow air and water vapor permeability which is not hindered by them being slanted at an angle or by the shape. At the same time the slanting and shaping will allow the capillaries to close under pressure excerpted from the wearer facing side on them such that liquid transport through the capillaries towards the outside of the article becomes nearly impossible. Hence these three-dimensional formed film layers are highly preferable in the context of breathable absorbent articles and in particular so with the additional second outer layer, which is provided as hereinafter explained.

The second outer layer of the breathable backsheet according to the present invention is a fibrous nonwoven web having a basis weight of less than 40 g/m2, preferably of less than 28 g/m2. More preferably, the second outer layer is a fibrous nonwoven web formed by a layered composite of a meltblown nonwoven layer made from synthetic fibers having a basis weight of less than 13 g/m2 and of a spunbonded nonwoven layer also made from synthetic fibers.

In the most preferred embodiment herein the backsheet comprises at least a first layer of a resilient, three dimensional web which consists of a liquid impervious polymeric film having apertures forming capillaries which are not perpendicular to the plane of the film but are disposed at an angle of less than 90° relative to the plane of the film, and at least a second breathable layer of a porous web which is a fibrous nonwoven composite web of a meltblown nonwoven layer made from synthetic fibers having a basis weight of less than 13 g/m2 and of a spunbonded nonwoven layer made from synthetic fibers.

Using as the breathable backsheet in the absorbent article of the present invention, a backsheet comprising at least one breathable layer of a resilient, three dimensional web which consists of a liquid impervious polymeric film having apertures forming capillaries which are not perpendicular to the plane of the film but are disposed at an angle of less than 90° relative to the plane of the film, and at least another breathable layer of a porous web which consists of a fibrous nonwoven web having a basis weight of less than 40 g/m2 (particularly of about 28 g/m2), further contributes to the outstanding benefit of the present invention. Indeed these backsheet functions very well in term of comfort, soiling of the user panty, dryness, etc. while providing additional comfort due to the reduced basis weight of the non-woven layer. This reduction of basis weight also provides an improved material consumption structure of the whole article.

Absorbent Core

According to the present invention, the absorbent can include the following components: (a) an optional primary fluid distribution layer preferably together with a secondary optional fluid distribution layer; (b) a fluid storage layer; (c) an optional fibrous ("dusting") layer underlying the storage layer; and (d) other optional components. According to the present invention the absorbent may have any thickness depending on the end use envisioned.

a Primary/Secondary Fluid Distribution Layer

One optional component of the absorbent core according to the present invention is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilized. The fluid distribution layers can be comprised of any material typical for such distribution layers. In particular fibrous layers maintain the capillaries between fibers even when wet are useful as distribution layers.

b Fluid Storage Layer

Positioned in fluid communication with, and typically underlying the primary or secondary distribution layers, is a fluid storage layer. The fluid storage layer can comprise the chitosan material and optional absorbent gelling material. It preferably comprises these materials in combination with suitable carriers.

Suitable carriers include materials, which are conventionally utilized in absorbent structures such as natural, modified or synthetic fibers, particularly modified or non-modified cellulose fibers, in the form of fluff and/or tissues. Most preferred are tissues or tissue laminates, for example air laid tissue laminate in the context of sanitary napkins and panty liners.

An embodiment of the absorbent structure made according to the present invention may comprise multiple layers comprises a double layer tissue laminate typically formed by folding the tissue onto itself. These layers can be joined to each other for example by adhesive or by mechanical interlocking or by hydrogen bridge bands. The chitosan material and optional absorbent gelling material and/or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

c Optional Fibrous ("Dusting") Layer

An optional component for inclusion in the absorbent core according to the present invention is a fibrous layer adjacent to, and typically underlying the storage layer. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Topsheet

According to the present invention the topsheet may comprise a single layer or a multiplicity of layers. In a preferred embodiment the topsheet comprises a first layer, which provides the user-facing surface of the topsheet and a second layer between the first layer and the absorbent structure/core. The topsheet provides a layer through which the liquids to be absorbed penetrate to the absorbent material.

The topsheet as a whole and hence each layer individually needs to be compliant, soft feeling, and non-irritating to the wearer's skin. It also can have elastic characteristics allowing it to be stretched in one or two directions. Typically, the topsheet extends across the whole of the absorbent structure and can extend into and form part of or all of the preferred side flaps, side wrapping elements or wings. According to the present invention the topsheet may be formed from any of the materials available for this purpose and known in the art, such as woven non woven materials, polymeric materials such as apertured formed thermoplastic films, apertured plastic films and hydro formed thermoplastic films, thermoplastic scrims or combinations thereof. Suitable woven and non-woven materials can be comprised of natural fibers (e.g., wood or cotton fibers), synthetic fibers (e.g., polymeric fibers such as polyester, polypropylene or polyethylene fibers) or from a combination of natural and synthetic fibers or bi-/multi-component fibers and are preferably hydrophobic.

In a preferred embodiment of the present invention at least one of the layers of the topsheet comprises a hydrophobic, liquid permeable apertured polymeric film. Preferably, the upper layer is provided by a film material having apertures which are provided to facilitate liquid transport from the wearer facing surface towards the absorbent structure, as detailed for example in U.S. Pat. No. 3,929,135, U.S. Pat. No. 4,151,240, U.S. Pat. No. 4,319,868, U.S. Pat. No. 4,324,426, U.S. Pat. No. 4,343,314, U.S. Pat. No. 4,463,045, U.S. Pat. No. 5,006,394 and U.S. Pat. No. 4,591,523. Apertured formed films are especially preferred for the topsheets because they are pervious to body exudates and yet non-absorbent and have a reduced tendency to allow fluids to pass back through and rewet the wearer's skin. Thus, the surface of the formed film that is in contact with the body remains dry; thereby reducing body soiling and creating a more comfortable feel for the wearer. Particularly preferred micro apertured formed film topsheets are disclosed in U.S. Pat. No. 4,609,518 and U.S. Pat. No. 4,629,643.

Topsheets having not a homogeneous distribution of liquid passageways but only a portion of the topsheet comprising liquid passageways are also contemplated by the present invention. Typically such topsheets would have the liquid passageways oriented such that they result in a centrally permeable and peripherally impermeable topsheet for liquids.

The wearer-facing surface of the formed film topsheet can be hydrophilic so as to help liquid to transfer though the topsheet faster than if the body surface was not hydrophilic. In a preferred embodiment, surfactant is incorporated into the polymeric materials of the formed film topsheet such as is described in WO 93/09741. Alternatively, the wearer-facing surface of the topsheet can be made hydrophilic by treating it with a surfactant such as is described in U.S. Pat. No. 4,950,254.

According to the present invention the absorbent article is constructed by joining the various elements such as topsheet, backsheet and absorbent core by any means well known in the art. For example the backsheet and/or topsheet may be joined to the absorbent core or to each other by a uniform continuous layer of adhesive, a patterned layer of adhesive, or an array of separate lines, spirals or spots of adhesive. Alternatively, the elements may be joined by heat bonds, pressure bonds, ultra sonic bonds, dynamic mechanical bonds or any other suitable joining means known in the art and any combination thereof. Preferably the breathable backsheet is bonded to other elements of the absorbent article so as to minimize and preferably eliminate any reduction in the vapor permeability of the backsheet.

According to the present invention the absorbent article may find utility as sanitary napkins, panty liners, adult incontinence products, nursing pads and baby diapers. The present invention finds particular susceptibility as sanitary napkins and panty liners. Thus in addition to the components described herein above, the absorbent article may also comprise all those features and parts which are typical for products in the context of their intended use such as wings and side flaps, undergarment adhesive means, release paper, wrapping elements, fastening means and the like.

Air Permeability Test

The air permeability test is utilized to assess the ability of an absorbent article to circulation/exchange air.

Basic Principle of the Methods:

The basic principle of the test is to evaluate the resistance of an absorbent article to the passage of air. In this test, the volume (or amount) of air that flows through an article to be tested of given dimensions under standard conditions (of 23° C./50% RH) is measured. The instrument utilized for the test is: Air Permeabilimeter FX 3300 manufactured by TexTest AG Switzerland.

Air Permeability for Dry Article

Samples should be allowed to equilibrate in the test environment for at least 4 hrs prior to commencement of the measurement. The article (having dimensions exceeding 5 $cm^2$ the dimensions of the measurement head) is placed on the device as instructed by the manufacturer. An aspiration pump set to generate a pressure of 1210 kPa that sucks air through the sample layer or structure. The device measures the volume of airflow and the pressure drop across the orifices that contain the sample and measurement head. Finally the device generates a value of air permeability in the units of liters/m2/s.

Air Permeability for Wetted Article

The basic principle of the test is to evaluate the air permeability performance of the article in presence of liquid, which simulates bodily discharges. To ensure that this test is sufficiently representative to the situation when the absorbent article is actually used a test solution closely resembling human menses is utilized, referred to herein as Artificial Menstrual Fluid (AMF). AMF is based on modified sheep's' blood as detailed in the solution preparation method detailed below.

Samples should be allowed to equilibrate in the test environment for at least 4 hrs prior to commencement of the measurement. Than 2 ml of test solution (AMF) should be applied on the center of the test article samples (which have dimensions exceeding 5 $cm^2$ the dimensions of the measurement head) than the samples should be placed on the device as instructed by the manufacturer. An aspiration pump set to generate a pressure of 1210 kPa that sucks air through the sample layer or structure. The device measures the volume of airflow and the pressure drop across the orifices that contain the sample and measurement head. Finally the device generates a value of air permeability in the units of liters/m2/s.

Preparation of Test Liquid AMF

Artificial Menstrual Fluid (AMF) is based on modified sheep's blood that has been modified to ensure it closely resembles human menstrual fluid in viscosity, electrical conductivity, surface tension and appearance. In addition we introduce a surfactant (1%) to this test fluid (supplied by Pegesis/USA) to better reflect stress situations in which typical hygiene practice (and in some limited situations, dietary influences) may introduce additional surfactants or unexpected levels of, for example, fatty acids, that might lower the blood surface tension. Low surface tension menses is the biggest contributor to through backsheet wet-through failure on a breathable absorbent article such as a sanitary article.

Reagents:
1) Difibrinated sheep's blood is available from Unipath S.p.A {Garbagnate Milanese/Italy}.
2) Lactic Acid from J. T. Baker Holland Reagent Grade (85–95% w/w)
3) Potassium Hydroxide (KOH) from Sigma Chemical Co. USA, Reagent grade
4) Phosphate Buffer Saline Tablets from Sigma Chemical Co. USA, Reagent grade
5) Sodium Chloride from Sigma Chemical Co. USA, Reagent grade
6) Gastric Mucine from Sigma Chemical Co. USA, Type III (CAS 84082-64-4)
7) Distilled Water.

Step 1:
Prepare a 9±1% Lactic Acid Solution by dissolution of lactic acid powder and distilled water.

Step 2:
Prepare a 10% Potassium Hydroxide (KOH) solution by dissolving KOH powder into distilled water.

Step 3:
Prepare a Phosphate buffer solution buffered to pH=7.2 by dissolving tablets as directed into 1 L distilled water.

Step 4:
Prepare and slowly heat to 45±5° C. a solution of the following composition:
460±5 ml of phosphate buffer solution
7.5±0.5 ml of KOH solution Step 5:
Prepare a Mucous Solution by slowly dissolution (with constant stirring) of approximately 30 grams of gastric mucine in the pre-heated (45±5° C.) solution prepared in step 4. Once dissolved the solution temperature should be increased to between 50–80° C. and the mixture covered for approximately 15 min. Turn the heat down to maintain a relatively constant temperature between 40 and 50° C. and continue to stir for a period of 2.5 hrs.

Step 6:
Remove the solution from the hot plate and allow the solution (from step 5) to now cool to less than 40° C. Add 2.0 ml of the 10% lactic acid solution and mix thoroughly for 2 min.

Step 7:
Place the solution in an Autoclave and heat to a temperature of 121° C. for 15 min.

Step 8:
Allow the solution to cool to room temperature and dilute 1 to 1 with the di-fibrinated sheep's blood.

Following AMF preparation its viscosity, pH and conductivity are measured to ensure the blood characteristics lie in a range close to that of normal menstrual blood {(see reference H. J. Bussing "zur Biochemie de Menstrualblutes" Zbl Gynaec, 179,456 (1957)}. The viscosity should lie in the range of 7 to 8 (units cStK). The pH should lie in the range of 6.9 to 7.5 and the conductivity in the range 10.5 to 13 (units mmho). If the viscosity is not within the range specified above it should not be used and a new batch of AMF needs to be prepared. This may require adjustment to the quantity of gastric mucine used. Since this is a natural product its composition may alter from one lot to another.

For individual measurements typically 100 ml AMF test solution with surfactant is prepared by mixing 90 ml AMF solution (maintained at 25° C.) with 10 ml Surfactant. The AMF/1% surfactant solution must be constantly mixed to ensure the components do not separate prior to usage. The solution should be used only within 4 hours of preparation.

According to the present invention the air permeability for the wet article (according to the measurement using 2 ml of AMF as described herein before) is at least 35%, preferably at least 45% of the air permeability of the dry article. It is understood that in this test the same articles are used to test their air permeability in both dry and wet conditions as described herein above.

The present invention is further illustrated by the following examples

EXAMPLES

Example 1

Pantiliners were prepared by modifying panty liners commercially available, namely "Alldays Duo Active" manufactured by Procter & Gamble, Germany. The topsheet is a film/non woven composite {film supplier code BPC 5105 CPM BP Chemical Germany, non-woven supplier code ARBO TB/BI Mequinenza Spain}. The core material is a tissue laminate (13.2 cm×4.0 cm) composed of a 2 layers of air laid tissue of 55 g/m² basis weight {available from Unikay Italy under the supplier code Unikay 303 LF}. Between the two tissue layers the laminate contains a chitosan material. The chitosan material is chitosonium pyrrolidone carboxylate powder, commercially available from Amerchol Corporation, Edison, N.J. under the name Kytamer® PC, at a basis weight of 2 g/m2.

The backsheet comprises two layers a first layer and a second layer. The first layer (also called secondary backsheet) is in contact with the absorbent tissue and the second layer. The second layer is in contact with the first layer and the undergarment of the wearer. The first layer is a formed apertured film (CPT) made of Low Density PE {supplied by Tredegar Film Products B.V. Holland under the manufacturing code X-1522}. The second layer is composed of a nonwoven laminate {13 MB/16 SB manufactured by Corovin GmbH in Germany under the trade name MD 2005}. The nonwoven laminate is composed of 16 g/m² spun bond and 13 g/m² meltblown. Each backsheet layer is joined over the full surface by an extensively overlapped spiral glue application at a basis weight of approximately 8 g/m². The glue utilized for attachment of both backsheet layers was supplied by SAVARE' SpA. Italy (under the material code PM17).

Figure 1:
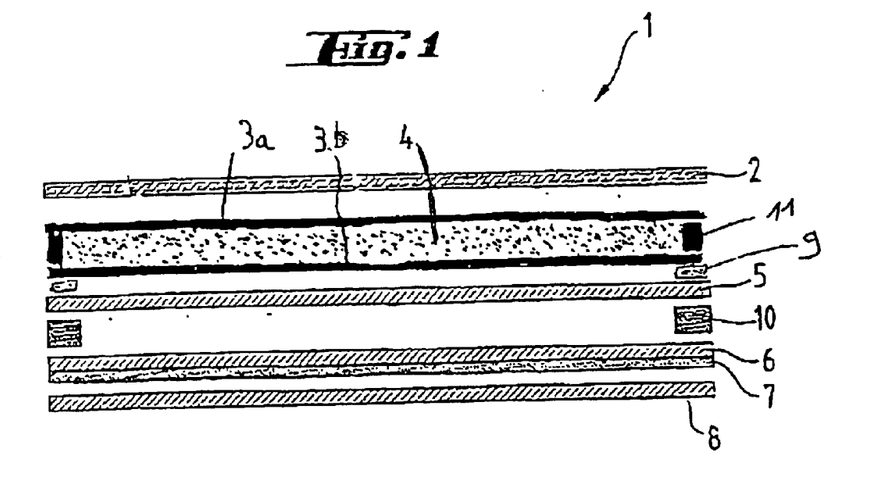
FIG. 1 shows a cross sectional view of a pantiliner having a topsheet, a breathable backsheet and an absorbent core comprising a first and a second tissue layers forming a laminate, the chitosan material is incorporated between said first and second tissue layers.

FIG. 1 represents a sectional view of a pantiliner structure 1 of Example 1 which comprises a topsheet 2, a first and a second air laid tissue layers 3a and 3b joined at their longitudinal edges with adhesive area 11, chitosonium pyrrolidone carboxylate powder 4 located between the air laid tissue layers 3a and 3b, a backsheet comprising a first layer 5 and a second layer 6, adhesive area 9 and 10, an adhesive layer 7 and a removable release liner 8.

Example 2

Example 2 is identical to Example 1 except that the chitosan material is a chitosan solution that is sprayed on the tissue air laid layers of the laminate core directed towards the backsheet. The chitosan solution can be sprayed on either side of the tissue air laid layer or even on both sides before reconstituting the pantiliner.

The chitosan solution is prepared by solubilizing 1 g of chitosonium pyrrolidone carboxylate commercially available from Amerchol Corporation under the name Kytamer® PC in 100 g of distilled water and stirring at 40° C. over 1 night. 10 g of the prepared solution are sprayed onto the tissue layer of the laminate to be position next to the backsheet.

Alternatively the chitosan material can be sprayed on the first layer of the backsheet (also called secondary backsheet) and the laminate core is free of chitosan.

Figure 2:
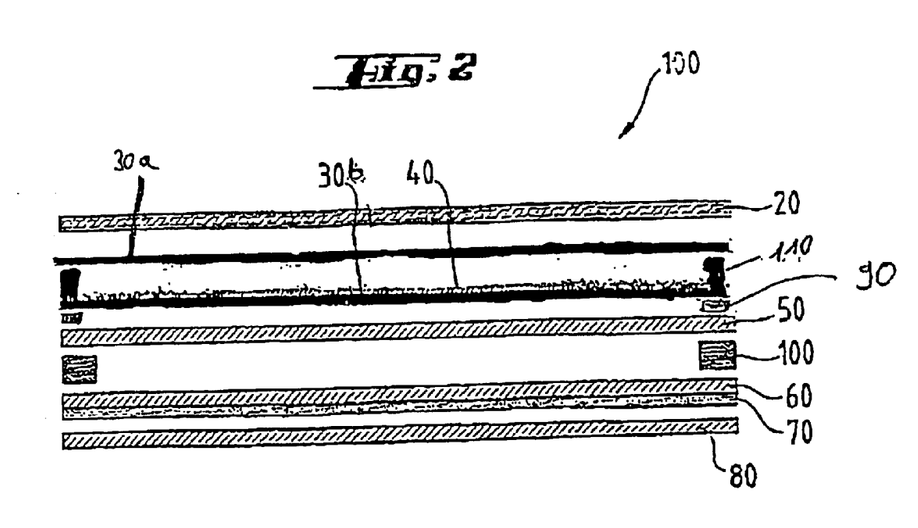
FIG. 2 shows a cross sectional view of a pantiliner having a topsheet, a breathable backsheet and an absorbent core comprising a first and a second tissue layers, wherein the chitosan material is located on the inner side of the second tissue layer.

FIG. 2 represents a sectional view of a pantiliner structure 100 of Example 2 which comprises a topsheet 20, a first and second air laid tissue layers 30a and 30b joined at their longitudinal edges with adhesive area 110, chitosonium pyrrolidone carboxylate 40 located on the inner surface of the second air laid tissue layer 30b, a backsheet comprising a first layer 50 and a second layer 60, adhesive area 90 and 1000, an adhesive layer 70 and a removable release liner 80.

Example 3

Example 3 is identical to example 1 except that the second layer of the backsheet has been replaced by a nonwoven laminate composed of 16 g/m² spun bond and 6 g/m² meltblown {supplied under the code of SM 22-6PH by Union SpA, Italy}.

Example 4

Example 4 is identical to example 2 except that the second layer of the backsheet has been replaced by a nonwoven laminate composed of 16 g/m² spun bond and 6 g/m² meltblown {supplied under the code of SM 22-6PH by Union SpA, Italy}.

Example 5

Example 5 is identical to example 1 except that absorbent gelling material (AGM) is added between the two tissue layers of the laminate on top of the chitosan material. The AGM added is cross-linked sodium polyacrylate available from DOW Chemicals Germany under the supplier code DOW XZ 9589001, at a basis weight of 30 g/m².

Figure 3:
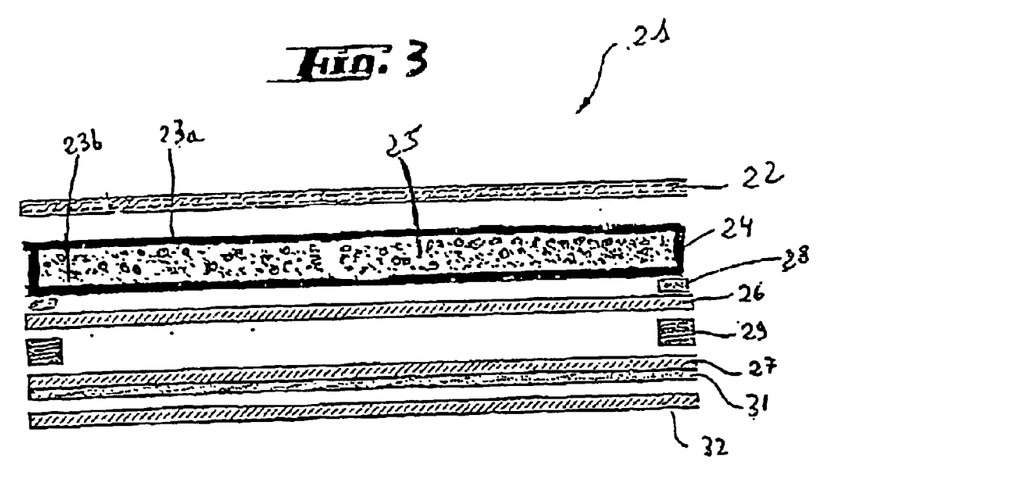
FIG. 3 shows a cross sectional view of a pantiliner having a topsheet, a breathable backsheet and an absorbent core comprising a first and a second tissue layers, wherein chitosan material together with absorbent gelling material are located between said first and second tissue layers.

FIG. 3 represents a sectional view of a pantiliner structure 21 of Example 5 which comprises a topsheet 22, a first and a second air laid tissue layers 23a and 23b joined at their longitudinal edges with adhesive area 24, a mixture 25 of chitosonium pyrrolidone carboxylate powder and absorbent gelling material powder located between the air laid tissue layers 23a and 23b, a backsheet comprising a first layer 26 and a second layer 27, adhesive area 28 and 29, an adhesive layer 31 and a removable release liner 32.

Example 6

Example 6 is identical to example 2 except that absorbent gelling material (AGM) is added between the two tissue layers of the laminate before reconstituting the pantiliner. The cross-linked sodium polyacrylate available from DOW Chemicals Germany under the supplier code DOW XZ 9589001, at a basis weight of 30 g/m² between the two tissue layers the laminate.

Figure 4:
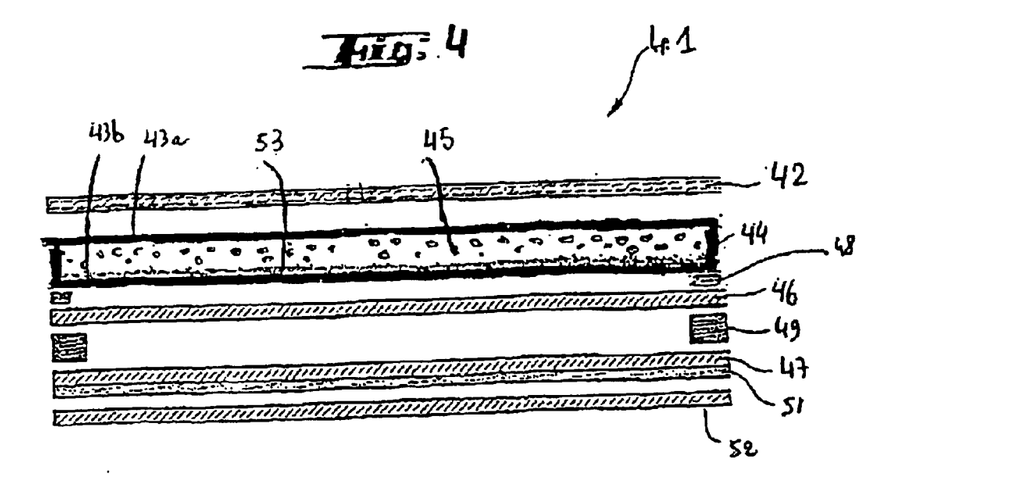
FIG. 4 shows a cross sectional view of a pantiliner having a topsheet, a breathable backsheet and an absorbent core comprising a first and a second tissue layers, wherein the absorbent gelling material are distributed between the first and second tissue layers and wherein chitosan material is applied onto the inner surface of the second tissue layer.

FIG. 4 represents a sectional view of a pantiliner structure 41 of Example 6 which comprises a topsheet 42, a first and a second air laid tissue layers 43a and 43b joined at their longitudinal edges with adhesive area 44, absorbent gelling material particles 45 located between the first and second air laid tissue layers 43a and 43b, chitosonium pyrrolidone carboxylate 53 located on the inner surface of the second air laid tissue 43b, a backsheet comprising a first layer 46 and a second layer 47, adhesive area 48 and 49, an adhesive layer 51 and a removable release liner 52.

Example 7

Example 7 is identical to example 5 except that the second layer of the backsheet has been replaced by a nonwoven laminate composed of 16 g/m² spun bond and 6 g/m² meltblown {supplied under the code of SM 22-6PH by Union SpA, Italy}.

Example 8

Example 8 is identical to example 6 except that the second layer of the backsheet has been replaced by a nonwoven laminate composed of 16 g/m² spun bond and 6 g/m² meltblown {supplied under the code of SM 22-6PH by Union SpA, Italy}.

Example 9

This is an example of a sanitary napkin according to the present invention. The sanitary napkin is based on an Always Ultra sanitary napkin available from Procter & Gamble Germany, which has been modified. The topsheet is a CPM material available from Tredegar Film Products B.V. Holland under the code X-1522. The core material is a tissue laminate (20.7 cm×7.0 cm) composed of a 2 layers of air laid tissue of 55 g/m² basis weight {available from Unikay Italy under the supplier code Unikay 303 LF}. Between the two tissue layers the laminate contains AGM (available from DOW Chemicals Germany under the supplier code; DOW XZ 95890.1) at a basis weight of 60 g/m², zeolite (available from Degussa Germany under the supplier code; Wessalith CS) at a basis weight of 61 g/m², silicate (available from Grace GmbH under the supply code Silica gel 123 or Syloblanc 82) at a basis weight of 61 g/m² and chitosonium pyrrolidone carboxylate, commercially available from Amerchol Corporation, Edison, N.J. under the name Kytamer® PC, at a basis weight of 10 g/m2.

The sanitary napkin has a multi-layer breathable backsheet comprising a formed apertured film backsheet layer and a second nonwoven layer. The first layer is a blend of low and high density PE with a crush resistant hexagonal hole configuration {supplied by Tredegar Film Products B.V. Holland under the manufacturing code AS 225 HD 25}. The second layer is an improved nonwoven laminate composed of 3 layers with basis weights 14 g/m² spun bond—20 g/m² meltblown—14 g/m² spun bond (manufactured by Corovin GmbH in Germany under the trade name MD 3005).

Example 10

Example 10 is identical to example 9 except that the second layer of backsheet has been replaced by a microporous layer (manufactured by Exxon Chemical Company in Illinois under the name Exxon XBF 112W) composed of Low Density PE and calcium carbonate particles at basis weight of 35 g/m2.

Example 11

Example 11 is identical to example 9 except that the first layer of backsheet has been replaced by an improved resilient tri-dimensional web (supplied by Tredegar Film Products B.V. Holland under the manufacturing code V174LD40) which consist of a blend of low density PE having apertures forming capillaries which are not perpendicular to the plane of the film but are disposed at an angle of less than 90° relative to the plane of the film and that the second layer of the backsheet has been replaced by a nonwoven laminate manufactured by Corovin GmbH (BBA Group) in Germany under the manufacturing code V 8/6. The nonwoven laminate is composed of 16 g/m² basis weight spun bond fiber layer and 11.5 g/m² basis weight meltblown fiber layer (thus a total basis weight of 27.5 g/m2).

Example 12

This is a further example of a sanitary napkin according to the present invention. The sanitary napkin is based on an Always Ultra sanitary napkin available from Procter & Gamble Germany, which has been modified. The topsheet is a CPM material available from Tredegar Film Products B.V. Holland under the code X-1522. The core material is a tissue laminate (20.7 cm×7.0 cm) composed of a 2 layers of air laid tissue of 55 g/m² basis weight {available from Unikay Italy under the supplier code Unikay 303 LF}. Between the two tissue layers the laminate contains AGM (available from DOW Chemicals Germany under the supplier code; DOW XZ 95890.1) at a basis weight of 60 g/m², zeolite (available from Degussa Germany under the supplier code; Wessalith CS) at a basis weight of 61 g/m², silicate (available from Grace GmbH under the supply code Silica gel 123 or Syloblanc 82) at a basis weight of 61 g/m².

A chitosan solution is sprayed on the air laid tissue layer of the laminate directed towards the backsheet. The chitosan solution is prepared by solubilizing 1 g of chitosonium pyrrolidone carboxylate commercially available from Amerchol Corporation under the name Kytamer® PC in 100 g of distilled water and stirring at 40° C. over 1 night. 10 g of the prepared solution is sprayed onto the tissue layer of the laminate to be position next to the backsheet on either side thereof or on both sides thereof.

The sanitary napkin has a multi-layer breathable backsheet comprising a formed apertured film backsheet layer and a second nonwoven layer. The first layer is a blend of low and high density PE with a crush resistant hexagonal hole configuration {supplied by Tredegar Film Products B.V. Holland under the manufacturing code AS 225 HD 25}. The second layer is an improved nonwoven laminate composed of 3 layers with basis weights 14 g/m² spun bond—20 g/m² meltblown—14 g/m² spun bond (manufactured by Corovin GmbH in Germany under the trade name MD 3005).

Example 13

Example 13 is identical to example 12 except that the second layer of backsheet has been replaced by a microporous layer (manufactured by Exxon Chemical Company in Illinois under the name Exxon XBF 112W) composed of Low Density PE and calcium carbonate particles at basis weight of 35 g/m2.

Example 14

Example 14 is identical to example 12 except that the first layer of backsheet has been replaced by an improved resilient tri-dimensional web (supplied by Tredegar Film Products B.V. Holland under the manufacturing code V174LD40) which consist of a blend of low density PE having apertures forming capillaries which are not perpendicular to the plane of the film but are disposed at an angle of less than 90° relative to the plane of the film and that the second layer of the backsheet has been replaced by a nonwoven laminate manufactured by Corovin GmbH (BBA Group) in Germany under the manufacturing code V 8/6. The nonwoven laminate is composed of 16 g/m² basis weight spun bond fiber layer and 11.5 g/m² basis weight meltblown fiber layer (thus a total basis weight of 27.5 g/m2).

Other examples of sanitary napkins are prepared similar to the ones in Examples 12, 13 and 14 except that the chitosan solution is sprayed on the first layer of the backsheet (also called secondary backsheet) and the core laminate is free of chitosan.

What is claimed is:

1. An absorbent article suitable for absorbing bodily fluid comprising a liquid permeable topsheet, a breathable backsheet and an absorbent core, said core being intermediate said topsheet and said backsheet, said article comprising from about 0.5 g/m² to about 500 g/m² of a chitosan salt.

2. An article according to claim 1 wherein the chitosan salt has a degree of deacetylation of more than 75%.

3. An article according to claim 2 wherein the chitosan salt has a degree of deacetylation from about 80% to about 100%.

4. An article according to claim 1 wherein the chitosan salt is selected from the group consisting of chitosan salt of citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid, thioglycolic acid, alanine, valine, leucine, isoleucine, prolinephenylalanine, glycine, serine, cysteine, tyrosine, asparagine, glutamine, lysine, arginine, hydroxyproline, pyrrolidone carboxylic acid, chitosonium pyrrolidone carboxylate and mixtures thereof.

5. An article according to claim 1, further comprising an absorbent gelling material or a mixture thereof.

6. An article according to claim 5, wherein the absorbent gelling material is a synthetic anionic absorbent gelling material or a mixture thereof.

7. An article according to claim 5, wherein the level of the absorbent gelling material or a mixture thereof is from about 5 g/m$^2$ to about 250 g/m$^2$.

8. An article according to claim 5, wherein the level of the absorbent gelling material or a mixture thereof is from about 7 g/m$^2$ to about 150 g/m$^2$.

9. An article according to claim 5 wherein the absorbent gelling agent is located in the absorbent article such that the bodily fluid first contacts the absorbing gelling material before contacting the chitosan salt.

10. An article according to claim 5 wherein the absorbent core comprises a tissue laminate comprising two opposite tissue layers, one facing the topsheet and one facing the backsheet, said tissue laminate comprising the chitosan salt and absorbant gelling material disposed between said two tissue layers, wherein the chitosan salt is directed towards the backsheet.

11. An absorbent article according to claim 1, further comprising at least an additional odor control agent.

12. An article according to claim 11, wherein said additional odor control agent is selected from the group consisting of silicas, zeolites, diatomaceous earth, carbons, starches, cyclodextrine, kieselguhr, clays, ion exchange resins, acids, masking agents, chelating agents, pH buffering means and combination thereof and preferably is silicate, zeolite or a combination thereof.

13. An article according to claim 11, which comprises from about 5 g/m$^2$ to about 600 g/m$^2$ of said additional odor control agent.

14. An article according to claim 5, further comprising at least an additional odor control agent.

15. An article according to claim 11, wherein said additional odor control agent is selected from the group consisting of silicas, zeolites, diatomaceous earth, carbons, starches, cyclodextrine, kieselguhr, clays, ion exchange resins, acids, masking agents, chelating agents, pH buffering means and combination thereof.

16. An article according to claim 1 wherein said breathable backsheet comprises at least one layer selected from an apertured polymeric film or a 2-dimensional planar apertured film.

17. An article according to claim 16, wherein said layer is a 2 dimensional planar apertured layer, wherein said apertures have an average diameter of from 150 micrometers to 5 micrometers.

18. An article according to claim 16, wherein said layer is an apertured polymeric film, wherein said apertures have an average diameter of from 100 micrometers to 500 micrometers.

19. An article according to claim 16, wherein said breathable backsheet comprises at least two layers, a first layer comprising an apertured layer and a second layer comprising a fibrous layer.

20. An article according to claim 19, wherein said breathable backsheet comprises at least a first layer of a resilient, three dimensional web which consists of a liquid impervious polymeric film having apertures forming capillaries which are not perpendicular to the plane of the film but are disposed at an angle of less than 90° relative to the plane of the film, and at least a second breathable layer being a fibrous nonwoven web made from synthetic fibers having a basis weight of less than 40 g/m$^2$.

21. An article according to claim 1 wherein said article is a sanitary napkin, a nursing pad, baby diaper or a panty liner.

22. An absorbent article suitable for absorbing bodily fluid comprising a liquid permeable topsheet, a breathable backsheet and an absorbent core, said core being intermediate said topsheet and said backsheet, said article comprising from about 0.5 g/m$^2$ to about 500 g/m$^2$ of a chitosan salt wherein the breathability of said article measured by its air permeability rate in l/m$^2$/s through the article thickness when subjected to 2 ml of artificial menstrual fluid is at least 35% of the air permeability of the dry article.

23. An absorbent article suitable for absorbing bodily fluid comprising a liquid permeable topsheet, a breathable backsheet and an absorbent core, said core being intermediate said topsheet and said backsheet, said article comprising from about 0.5 g/m$^2$ to about 500 g/m$^2$ of a chitosan salt.

24. The article of claim 23 wherein the chitosan salt is selected from the group consisting of chitosan salt of citric acid, formic acid, acetic acid, N-acetylglycine, acetylsalicylic acid, fumaric acid, glycolic acid, iminodiacetic acid, itaconic acid, lactic acid, maleic acid, malic acid, nicotinic acid, salicylic acid, succinamic acid, succinic acid, ascorbic acid, aspartic acid, glutamic acid, glutaric acid, malonic acid, pyruvic acid, sulfonyldiacetic acid, benzoic acid, epoxysuccinic acid, adipic acid, thiodiacetic acid, thioglycolic acid, alanine, valine, leucine, isoleucine, prolinephenylalanine, glycine, serine, cysteine, tyrosine, asparagine, glutamine, lysine, arginine, hydroxyproline, pyrrolidone carboxylic acid, chitosonium pyrrolidone carboxylate and mixtures thereof.

* * * * *